United States Patent
Robinson et al.

(10) Patent No.: US 11,771,528 B1
(45) Date of Patent: Oct. 3, 2023

(54) IMPLANT WITH ENHANCED OSTEOINDUCTIVITY

(71) Applicant: Spectrum Spine IP Holdings, Inc., Inlet Beach, FL (US)

(72) Inventors: James C. Robinson, Inlet Beach, FL (US); Timothy Ganey, Tampa, FL (US)

(73) Assignee: Spectrum Spine IP Holdings, LLC, Inlet Beach, FL (US)

( * ) Notice: Subject to any disclaimer, the term of this patent is extended or adjusted under 35 U.S.C. 154(b) by 0 days.

(21) Appl. No.: 17/942,420

(22) Filed: Sep. 12, 2022

(51) Int. Cl.
*A61C 8/02* (2006.01)
*A61C 13/00* (2006.01)
*A61C 8/00* (2006.01)

(52) U.S. Cl.
CPC .......... *A61C 8/0006* (2013.01); *A61C 8/0012* (2013.01); *A61C 13/0018* (2013.01); *A61C 2008/0046* (2013.01)

(58) Field of Classification Search
CPC ........ A61C 8/00–0096; A61C 13/0018; A61C 2008/0046; A61F 2/44
See application file for complete search history.

(56) References Cited

U.S. PATENT DOCUMENTS

| | | | |
|---|---|---|---|
| 4,608,052 A | 8/1986 | Van Kampen et al. | |
| 4,723,913 A * | 2/1988 | Bergman | A61C 8/0074 433/173 |
| 5,219,361 A | 6/1993 | Von Recum et al. | |
| 5,282,861 A | 2/1994 | Kaplan | |
| 5,490,962 A | 2/1996 | Cima | |
| 5,665,118 A | 9/1997 | Lasalle et al. | |
| 5,714,103 A | 2/1998 | Bauer et al. | |
| 6,129,872 A | 10/2000 | Jang | |
| 7,250,550 B2 | 7/2007 | Overby et al. | |
| 7,951,412 B2 | 5/2011 | Justin et al. | |
| 7,955,512 B2 | 6/2011 | Park et al. | |
| 10,398,559 B2 | 9/2019 | Jones et al. | |
| 10,500,059 B2 | 12/2019 | Grotz | |
| 10,561,456 B2 | 2/2020 | Cawley et al. | |
| 10,575,965 B2 | 3/2020 | Kim et al. | |
| 10,751,943 B2 | 8/2020 | Grbic et al. | |
| 10,786,874 B2 | 9/2020 | Guo et al. | |
| 2006/0293758 A1 * | 12/2006 | Yang | C23F 1/28 623/23.76 |

(Continued)

*Primary Examiner* — Yogesh P Patel
(74) *Attorney, Agent, or Firm* — David L. King

(57) ABSTRACT

An implant device configured to be at least partially in contact with bone on implantation has an improved osteoinductive feature to enhance new bone formation. The implant device has one or more bone growth surfaces extending from a structurally solid feature of the implant device. The one or more bone growth surfaces are configured to mimic adult trabecular bone by having trenches, grooves or surface recesses or prominences exhibiting numerous structural elements or walls not perpendicular to the surface that are non-coplanar or arched extending 20 to 500 microns in depth having an increasing inclination from the surface extending inwardly and not parallel to opposing or adjacent walls forming a random or non-random network. The one or more bone growth surfaces configured to mimic trabecular bone have discernable nano features on the structural elements or walls exhibiting nano scale features of less than 200 nano meters within the network.

8 Claims, 2 Drawing Sheets

(56) References Cited

U.S. PATENT DOCUMENTS

| | | | |
|---|---|---|---|
| 2007/0225785 A1 | 9/2007 | Park et al. | |
| 2008/0216926 A1 | 9/2008 | Guo et al. | |
| 2010/0003640 A1* | 1/2010 | Damstra | A61C 19/04 433/201.1 |
| 2013/0310948 A1 | 11/2013 | Luscher | |
| 2015/0209042 A1* | 7/2015 | Webster | A61P 19/04 606/151 |
| 2018/0256336 A1 | 9/2018 | Mueller et al. | |
| 2021/0330431 A1* | 10/2021 | Yang | A61C 8/0051 |
| 2022/0133443 A1* | 5/2022 | Lovera Prado | A61C 8/0071 433/174 |

* cited by examiner

IMPLANT WITH ENHANCED OSTEOINDUCTIVITY

FIELD OF THE INVENTION

The present invention relates to an implant device and a method of manufacturing an implant device with enhanced surfaces for bone growth formation.

BACKGROUND OF THE INVENTION

Implant devices that are embedded into bone are ideally secured to the bone by new bone growth formations that extend into the bone growth surfaces or adapt bone formation to that attaches to the implant device. Appreciation for the reciprocal responses between biologic tissues and material devices has focused on recreating specific environmental conditions that might best simulate a mechanistic approach to the mechanobiological response of cells. Such implant devices include bone screws and other bone fasteners, spinal fusion cages, plates used in bone fracture repairs, knee and hip repair devices, dental implant devices including abutments that when implanted into the jawbone at the gums and other devices used to stabilize bones for bone repair procedures exert physical effects that align and/or amplify normal biologic process. All of these devices are firmly secured to the bone by new bone growth that extends to and surrounds the bone growth surfaces of the implant device.

By way of example, one such device is a spinal implant. Surgical implantation of interbody cages is typically used to provide support along the spinal column in cases where a portion of the patient's intervertebral anatomy has become weakened, diseased, or destroyed. Such support systems are also commonly used following a discectomy, where an intervertebral disc is surgically removed.

Most commonly, existing support systems typically operate by inhibiting normal movement between the adjacent vertebrae, thereby stabilizing these vertebrae at fixed positions relative to one another, with the mechanical body of the supporting structure providing the needed support along the patient's spinal column. Such supporting systems are typically made of stainless steel, titanium, titanium alloy, polymer (e.g., an organic polymer thermoplastic such as polyether ether ketone (PEEK)), carbon fiber, ceramic, combinations such as metal-ceramic (Cermet), or combinations of ceramic and thermoplastic designed to permanently remain within the patient's body.

It is beneficial, in addition to fixation, to try to stimulate bone growth between the adjacent vertebrae. To do so, spine surgeons often use bone graft material in addition to fixation devices. Bone graft doesn't heal or fuse the spine immediately; instead, bone graft provides a foundation or scaffold for the patient's body to grow new bone. Not intended to be an impediment to motion, bone graft serves an inductive intention to stimulate new bone production. When new bone grows and solidifies, fusion occurs. Although instrumentation (e.g., screws, rods) is often used for initial stabilization (post-operative), it is the healing of bone that welds vertebrae together to create long-term stability. There are two general types of bone grafts: real bone and bone graft substitutes. Real bone can come from the patient (autograft) or from a donor bone (allograft). Also used in these types of surgery are bone substitute, osteoinductive agents, stem cell products, bone morphogeneic proteins, and bone cement.

There is a need for improved systems and methods for bone implant devices. Ideally, the bone implant device has features that facilitate new bone growth to achieve hastened attachment and fusion to the patient's bone. The present invention provides for an improved bone growth surface to enhance osteoinductivity for new bone growth formation.

Definitions

As used herein and in the claims:

A femtosecond laser is an infrared laser that emits bursts of laser energy at an extremely fast rate. A femtosecond laser has a pulse duration in the femtosecond range, or one quadrillionth of a second. A femtosecond laser is a laser that emits optical pulses with a duration well below 1 ps (→ultrashort pulses), i.e., in the domain of femtoseconds (1 fs=10-15 s). It thus also belongs to the category of ultrafast lasers or ultrashort pulse lasers (which also include picosecond lasers). Femtosecond (FS) laser is an infrared laser with varying wavelengths of 1053 nm that can be manipulated in pulse duration to attain optical bandwidth which scales with the inverse pulse duration; slight variation but if that limit is reached, one has so-called bandwidth-limited pulses that provide wavelength reciprocity Green lasers with the appropriate power required for industrial applications are usually frequency-doubled IR lasers with wavelengths between 515 nm and 532 nm. Their disadvantage is that they are—compared to the IR variants—less efficient, may lose power during a manufacturing process, and require expensive cooling and complex optical setups. The most common green lasers are actually infrared lasers, emitting natively 1064 nm light. There is a second crystal used to double the frequency, and half the wavelength down to 532 nm, providing green light. The infrared light should then be filtered out to get only green output. Wavelengths can vary from 470 to 570 nm depending on the application.

Laser texturing is an emerging technology for generating surface functionalities on basis of optical, mechanical, or chemical properties. Taking benefit of laser sources with ultrashort (fs) pulse durations features outstanding precision of machining and negligible rims or burrs surrounding the laser-irradiation zone. Consequently, additional mechanical or chemical post-processing steps are usually not required for fs-laser surface texturing (fs-LST). This work aimed to provide a bridge between research in the field of tribology and laser materials processing.

Nanotechnology is the engineering of functional systems at the nanometer scale. This covers both current work and concepts that are more advanced. In its original sense, nanotechnology refers to the projected ability to construct items from the bottom up, using techniques and tools being developed today to make complete, high-performance products. Alternatively, nanostructure may be developed through subtractive processes.

Cortical or compact bone can be distinguished macroscopically from cancellous or trabecular bone. Cortical bone is a dense tissue that contains less than 10% soft tissue. Cancellous or spongy bone is made up of trabeculae, shaped as interconnected plates or rods and arced structures interspersed between voids in the mineral structure that contain blood cells in the marrow space which represents more than 75% of the cancellous bone volume. The dividend inherent to the diverse shapes attending the macrostructure are emblematic in aligning cell responses onto those surface variations.

Microtechnology/Laser Micro Machining Although similar in concept to traditional machining operations, laser micro machining (laser micromachining) is capable of creating extremely small features—generally under 1 mm, and in some cases only a few microns in size—with a high degree of repeatability and without causing significant structural damage to the surrounding material. This advent of nano-sculpting also achieves an order of randomness as an inevitable consequence of the resolution of the machining precision which support the concept that nature and evolution of biological systems have thrived in distilling the distinction between purely random and partially random variation.

Micron (μm) Microns, also known as micrometers (represented as μm) are a length of measurement equal to one millionth of a meter. (1,000 μm is equal to 1 mm.)

Nanotechnology: One nanometer (nm) is one billionth, or $10^{-9}$, of a meter. By comparison, typical carbon-carbon bond lengths, or the spacing between these atoms in a molecule, are in the range 0.12-0.15 nm, and a DNA double-helix has a diameter around 2 nm. On the other hand, the smallest cellular life-forms, the bacteria of the genus Mycoplasma, are around 200 nm in length. By convention, nanotechnology is taken as the scale range 1 to 100 nm following the definition used by the National Nanotechnology Initiative in the US. The lower limit is set by the size of atoms (hydrogen has the smallest atoms, which are approximately a quarter of a nm kinetic diameter) since nanotechnology must build its devices from atoms and molecules. The upper limit is more or less arbitrary but is around the size below which the phenomena not observed in larger structures start to become apparent and can be made use of in the nano device. These new phenomena make nanotechnology distinct from devices which are merely miniaturized versions of an equivalent macroscopic device; such devices are on a larger scale and come under the description of microtechnology.

"Prominent" standing out or projecting beyond a surface or line: protuberant.

Trabecular bone is a highly porous (typically 75-95%) form of bone tissue that is organized into a network of interconnected walls, rods and plates and arcs called trabeculae which surround pores that are filled with cellular bone marrow.

SUMMARY OF THE INVENTION

An implant device and its method of manufacture configured to be at least partially in contact with bone on implantation has an improved osteoinductive feature to enhance new bone formation. The implant device has one or more bone growth surfaces extending from a structurally solid feature of the implant device. The one or more bone growth surfaces are configured to mimic adult trabecular bone by having trenches, grooves or surface recesses or prominences exhibiting numerous structural elements or walls not perpendicular to the surface that are non-coplanar or arched extending 20 to 500 microns in depth having an increasing inclination from the surface extending inwardly and not parallel to opposing or adjacent walls forming a random or non-random network. The one or more bone growth surfaces configured to mimic trabecular bone have discernable nano features on the structural elements or walls exhibiting nano scale or nano-meter scale features of less than 200 nanometers within the network.

An area of the one or more bone growth surfaces of the implant with the discernable nano features having a surface area always greater surface area than that at the surface of the structurally solid feature without the discernable nano features. In some embodiments, the area of the bone growth surface configured to mimic trabecular bone with the discernable nano features has a surface area 100 times or more a same size area of the surface of the structurally solid feature not configured with the discernable nano features.

The one or more bone growth surfaces are exposed to a laser beam having a power intensity wavelength of around 470-570 nano meters to create the trabecular bone mimicking features with discernable nano features in the one or more bone growth surfaces.

The implant can be made of a metal material, wherein the metal material when exposed to the laser exhibits an increased oxidation at the surface chemically altering the material to enhance osteoinductivity for new bone growth formation when implanted. The metal can be a titanium alloy and the metal when exposed to the laser is enhanced with titanium oxide. The titanium alloy is preferably made with 90 percent titanium, 6 percent aluminum and 4 percent vanadium and wherein the oxidation created by the laser alters the chemical structure at the surface by forming titanium oxide to enhance new bone growth.

The implant can also incorporate ceramics as part of its composition. A cermet can combine attractive properties of both a ceramic, such as high temperature resistance and hardness, and those of a metal, such as the ability to undergo plastic deformation. Depending on the physical structure of the material, cermets can also be considered as metal matrix composites, but cermets are usually less than 20% metal by volume.

Cermets have been used in the manufacture of resistors (especially potentiometers), capacitors, and other electronic components. In the context of biologic systems which are based on membrane polarization and nano-voltage, it is not surprising that Zirconia-titanium sintered constructs have been known for some time to enhance bone cell response.

In certain embodiments, the implant device is one of a spine implant for bone fusion between vertebrae, or a bone fastener, or an orthopedic device for implantation onto or into bone, or a dental implant device for implantation into the bone structure of a patient. When the device is a dental implant for tooth replacement, the dental implant is an abutment for implantation into the bone structure of the jawbone. Preferably, the one or more bone growth surfaces are produced by a subtraction laser etching process in which the surface of the implant has discernable features of structural elements having nano scale features at less than 200 nanometers. Etching or ablation of the solid results in decreasing the volume of the implant and increasing the surface area wherein the area treated shows increased surface area within a volumetric reduction.

BRIEF DESCRIPTION OF THE DRAWINGS

The invention will be described by way of example and with reference to the accompanying drawings in which.

DETAILED DESCRIPTION OF THE INVENTION

Figure 1:
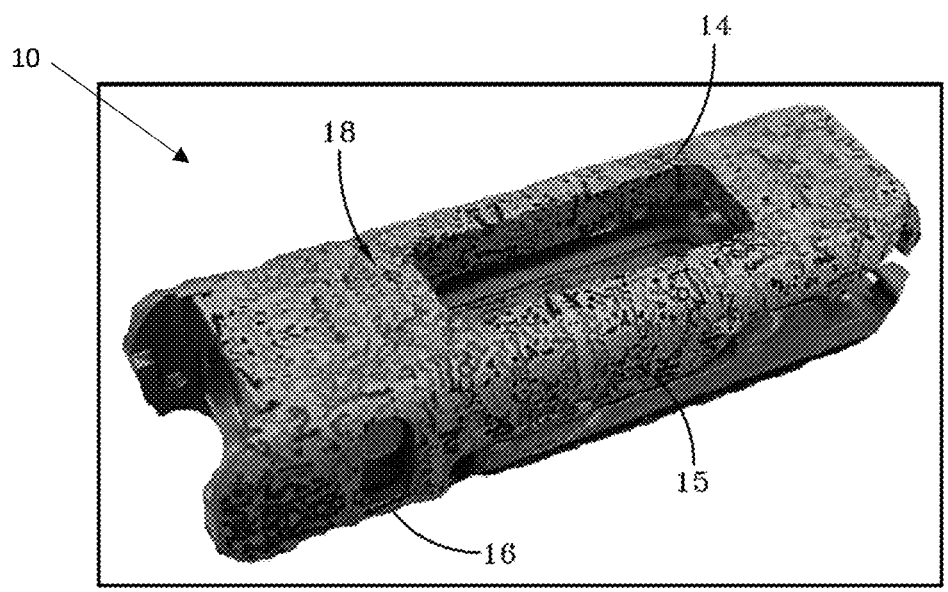
FIG. 1 is a perspective view of an expandable spinal implant device made according to the present invention.

With reference to FIG. 1, a perspective view of an exemplar device of an expandable spinal implant device 10 is shown having been made according to the present invention. As shown, side surfaces 14, 15, 16 have the feature for enhanced osteoinductivity for encouraging new bone to fuse to the device 10 after being installed in the disc space. The device 10 has an enhanced feature that creates a surface area 30 with nano features 32 for new bone growth formation to attach. These surface areas 30 include surfaces in contact with bone on implantation as well as surfaces where new bone growth on the sides of the device helps secure the device in place after bone fusion occurs. Each surface area 30 has nano features 32 shown in FIG. 3. The device 10, as shown, is in a partially expanded condition. The level of expansion can be raised to a higher amount or lowered to a closed position for insertion.

Figure 2:
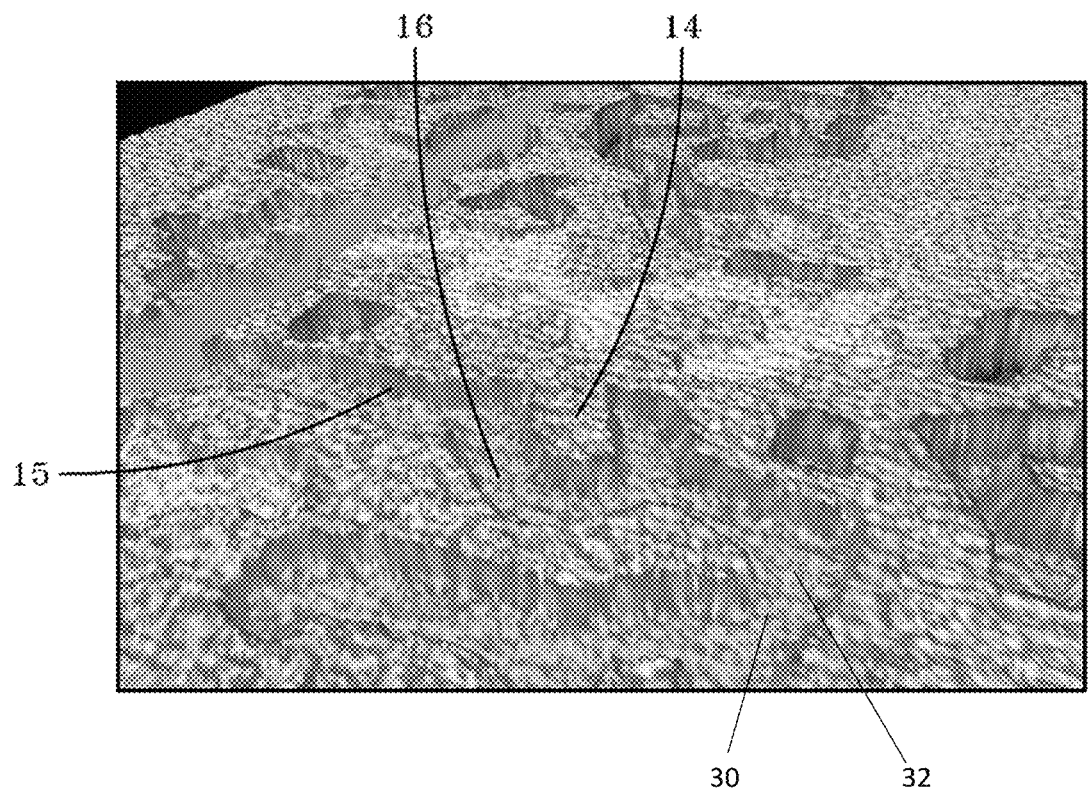
FIG. 2 is an enlarged view of a surface made using the process of the present invention.

The enlarged view of FIG. 2 illustrates the appearance of the trabecular bone mimicking surface area 30. The one or more bone growth surfaces 14, 15, 16 extending from a structurally solid feature of the implant device 10, wherein the one or more bone growth surfaces are configured to mimic adult trabecular bone by having trenches, grooves or surface recesses or prominences exhibiting numerous structural elements or walls not perpendicular to the surface that are non-coplanar or arched extending 20 to 500 microns in depth having an increasing inclination from the surface extending inwardly and not parallel to opposing or adjacent walls forming a random or non-random network 18 containing nano features 32.

Figure 3:
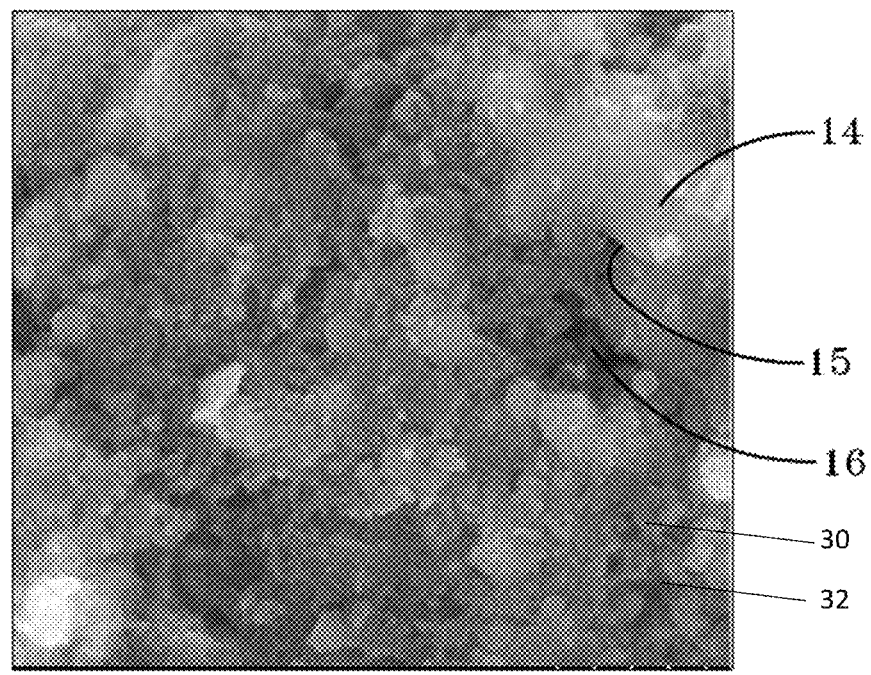
FIG. 3 is a magnification of the surface made using the process of the present invention.

FIG. 3 is a highly magnified image that shows the nano features 32 of the surface area 30 in which the entire width of the image shown is only about 2 microns. The scale can be appreciated in the image shown in FIG. 1 of the textured implant device 10 which is 35 mm in length and the trenches, grooves or surface recesses or prominences can be easily seen by eye without magnification. The nano features 32 are only visible through powerful magnification which affords sub-micron resolution. As shown, these nano features 32 exhibit very high surface areas in relation to their size. This large surface area creates advantageous regions to induce and to receive new bone growth. The bone-forming cells attach to these nano features 32 with greater ease and affinity than on solid untreated surfaces of the implant 10. The bone-forming cells become "activated" to form and remodel new bone through biologic changes in their morphology and chemistry due to their interaction with this unique surface structure. Activation is furthered by cell-cell communication, fostering a tissue based organization that evolves from a cell-based induction.

Figure 4:
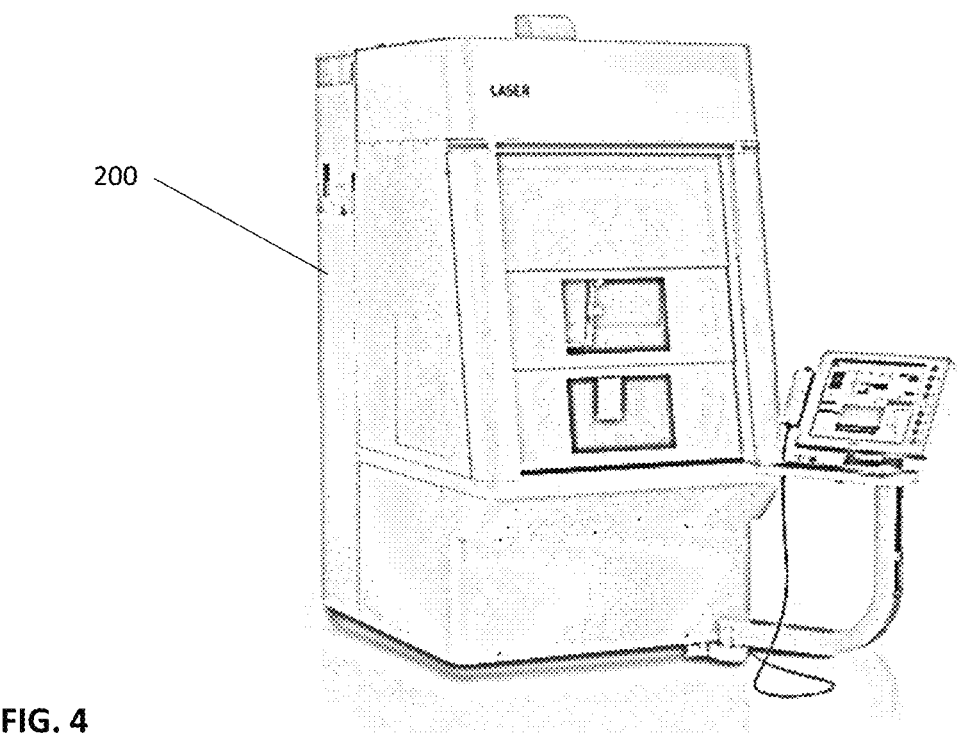
FIG. 4 is an exemplary laser device.

In FIG. 4, an exemplary laser etching machine 200 is illustrated that can be used to form bone growth enhancing features. These features can be laid in a network 18 of trenches, grooves or surface recesses or prominences or combinations thereof either in an organized uniform network pattern or a random non-uniform network pattern throughout the exterior surfaces 14, 15, 16. Ideally, these nano channels 30 are created at least along the first and second surfaces 14, 16 of the implant device 10. The nano channels 30 are the result of small laser etched cuts that can be laid out along the entire exterior surfaces in a subtractive laser etching process. These nano channels 30 created by laser etching can be made either by moving the laser 200 about the surface 14, 15, 16 of the implant device to form the nano channels 30; or the implant device 10 can be moved relative to the laser such that the nano channels 30 are laid onto the exterior surfaces 14, 15, 16. Or the process may move both the implant and the laser simultaneously. The nano features 32 individually create an improved osteoinductive effect at the surface of the implant device 10. While the network 18 can be uniform, the nano features 32 themselves are random having non-coplanar walls or arches with increasing inclination from the depth to the surface. This means that the formation of new bone once implanted into the patient can be accelerated and the network 18 of nano features 32 provide features that help assist in providing attachment locations for the new bone formation. This continuous and progressive architecture with Z-vector variation in addition to the macro-surface geometry is an important feature that is provided in the current invention and is ideal in that it does not require smooth or flat exterior surfaces to form the channels which are effectively etched into the exterior surface. The channels can be created as long as the path of the laser beam is unobstructed.

It is noted any implant device can be treated post manufacturing to create these surfaces on an existing implant device. Furthermore, the process can be used to form the surfaces on any number of implants where osteoinductive bone grown enhancement is desired. These can be bone fasteners, pedicle screws, cervical plates, spinal fusion cages, dental implants, non-spinal orthopedic implants and any bone growth implant device or bone-interfacing device that benefits from bone growth into and/or around the surface of the implant.

The materials the implant device 10 is made of can be any suitable implant material of metal, cermet, plastic or bone and the benefits of enhanced osteoinductivity can be achieved.

These and other aspects of the present invention are believed to greatly enhance the ability of the present device made by laser etching to provide an improved implant fusion device.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. An implant device configured to be at least partially in contact with bone on implantation having an improved osteoinductive feature to enhance new bone formation, the implant device comprising:

an implant device having a structurally solid feature;

one or more bone growth surfaces formed from the structurally solid feature of the implant device by subtractive laser etching, wherein the one or more bone growth surfaces are configured to mimic adult trabecular bone by having trenches, grooves or surface recesses or prominences exhibiting numerous structural elements or walls not perpendicular to the surface that are non-coplanar or arched extending 20 to 500 microns in depth having an increasing inclination from the surface extending inwardly and not parallel to opposing or adjacent walls forming a random or non-random network; and wherein the one or more bone growth surfaces configured to mimic adult trabecular bone have discernable nano scale prominences, the nano scale prominences projecting less than 200 nano meters from the one or more bone growth surfaces only visible through magnification of sub-micron resolution exhibiting large surface areas relative to the size of the nano scale prominences configured to enhance and receive new bone growth providing the improved osteoinductive feature and variations of surface features resulting from the manufacturing process and the material composition of the implant device, wherein an area of the one or more bone growth surfaces of the implant with the discernable nano scale prominences having a surface area greater with no additional volume than the surface area of the structurally solid feature without the discernable nano scale prominences and nano scale prominences at less than 200 nano meters that are formed by a subtraction laser etching process on the surface of the bone growth surfaces of the implant.

2. The implant device of claim 1, wherein the one or more bone growth surfaces is exposed to a laser beam having a power intensity wavelength of around 470-570 nano meters to create the trabecular bone mimicking features with discernable nano scale prominences in the one or more bone growth surfaces.

3. The implant device of claim 2, wherein the implant is made of a metal material or cermet or plastic or bone or any combination thereof.

4. The implant device of claim 3, wherein the implant when exposed to the laser exhibits an increased oxidation at the surface chemically altering the implant to enhance osteoinductivity for new bone growth formation when implanted.

5. The implant device of claim 3, wherein the metal is a titanium alloy and the metal when exposed to the laser is enhanced with metal oxide from the device.

6. The implant device of claim 5, wherein the titanium alloy is 90 percent titanium, 6 percent aluminum and 4 percent vanadium and wherein the oxidation created by the laser alters the chemical structure at the surface by forming titanium oxide, aluminum oxide or vanadium oxide to enhance new bone growth.

7. The implant device of claim 1, wherein the implant device is one of a spine implant for bone fusion between vertebrae, or a bone fastener, or an orthopedic device for implantation onto or into bone, or a dental implant device for implantation into the bone structure of a patient.

8. The implant device of claim 1, wherein the device is a dental implant for tooth replacement, the dental implant being an abutment for implantation into the bone structure of the jawbone.

* * * * *